(12) United States Patent
Andresen et al.

(10) Patent No.: US 8,500,894 B2
(45) Date of Patent: Aug. 6, 2013

(54) WET SCRUBBING FOR REMOVING PARTICULATE SOLIDS FROM OXYGEN SUPPLY LINE

(75) Inventors: Harvey E. Andresen, Luling, LA (US); Christopher P. Christenson, Lake Jackson, TX (US); Charles W. Lipp, Lake Jackson, TX (US); John R. Mayer, The Woodlands, TX (US); Thomas J. Kling, Midland, MI (US); Victor R. Fey, West Bloomingfield, MI (US); Laurence G. Britton, Charleston, WV (US); Michael J. Rangitsch, Saginaw, MI (US); Michael L. Hutchison, Poca, WV (US)

(73) Assignee: Dow Technology Investments LLC, Midland, MI (US)

( * ) Notice: Subject to any disclaimer, the term of this patent is extended or adjusted under 35 U.S.C. 154(b) by 524 days.

(21) Appl. No.: 12/678,263

(22) PCT Filed: Nov. 12, 2008

(86) PCT No.: PCT/US2008/012715
§ 371 (c)(1),
(2), (4) Date: Mar. 15, 2010

(87) PCT Pub. No.: WO2009/078900
PCT Pub. Date: Jun. 25, 2009

(65) Prior Publication Data
US 2010/0263535 A1  Oct. 21, 2010

Related U.S. Application Data

(60) Provisional application No. 61/007,671, filed on Dec. 14, 2007.

(51) Int. Cl.
*B01D 47/00* (2006.01)
*B01D 47/02* (2006.01)
*B01D 47/14* (2006.01)

(52) U.S. Cl.
USPC ............. 96/290; 96/322; 96/351; 96/355; 96/371; 95/230; 95/187; 95/195; 95/210

(58) Field of Classification Search
None
See application file for complete search history.

(56) References Cited

U.S. PATENT DOCUMENTS

| | | |
|---|---|---|
| 2,614,616 A | 10/1952 | Villoresi et al. |
| 2,981,747 A | 4/1961 | Lang et al. |

(Continued)

FOREIGN PATENT DOCUMENTS

| | | |
|---|---|---|
| DE | 102005020942 | 11/2006 |
| EP | 0006734 | 1/1980 |

(Continued)

OTHER PUBLICATIONS

PCT International Preliminary Report on Patentability, PCT International Application No. PCT/US2008/012716, mailed Jun. 24, 2010.

(Continued)

*Primary Examiner* — Duane Smith
*Assistant Examiner* — Pankti Patel
(74) *Attorney, Agent, or Firm* — McDonnell Boehnen Hulbert & Berghoff LLP

(57) ABSTRACT

A method of mixing an oxygen gas with a hydrocarbon-containing gas includes the steps of wet scrubbing the oxygen gas in a wet scrubber, supplying oxygen gas from the wet scrubber to a gas mixer and mixing the oxygen gas with the hydrocarbon-containing gas in the gas mixer. Wet scrubbers for use in the method may take various forms, including packed-tower, bubble cap, and sparger-type wet scrubbers. The removal of the particulate matter reduces the risk of ignition of the hydrocarbon-containing gas in the gas mixer. The use of a wet scrubber in the oxygen supply line overcomes many problems currently faced with screen and filters, as per current practice.

19 Claims, 3 Drawing Sheets

U.S. PATENT DOCUMENTS

| | | | |
|---|---|---|---|
| 2,998,465 A | | 8/1961 | Drummond et al. |
| 3,081,818 A | | 3/1963 | Braconier et al. |
| 3,237,923 A | | 3/1966 | Turner |
| 3,518,284 A | | 6/1970 | Foster |
| 3,570,471 A | | 3/1971 | Lazaridis |
| 3,702,619 A | * | 11/1972 | Son .................................. 137/3 |
| 3,706,534 A | | 12/1972 | Verheul et al. |
| 4,012,469 A | | 3/1977 | Accortt |
| 4,256,604 A | | 3/1981 | Aida et al. |
| 4,348,476 A | | 9/1982 | Hou |
| 4,390,346 A | | 6/1983 | Cramer et al. |
| 4,393,817 A | | 7/1983 | Lindberg |
| 4,415,508 A | * | 11/1983 | Aida et al. ................ 261/114.1 |
| 4,564,298 A | | 1/1986 | Gritters et al. |
| 4,573,803 A | | 3/1986 | Gritters et al. |
| 4,634,459 A | * | 1/1987 | Pischinger et al. ............ 55/418 |
| 4,926,620 A | * | 5/1990 | Donle ............................. 95/202 |
| 5,037,619 A | | 8/1991 | Alagy et al. |
| 5,178,654 A | | 1/1993 | Cowley |
| 5,250,267 A | | 10/1993 | Johnson et al. |
| 5,328,359 A | | 7/1994 | Retallick |
| 5,336,791 A | | 8/1994 | Jennings et al. |
| 6,231,648 B1 | * | 5/2001 | Marlowe ........................ 96/243 |
| 6,657,079 B1 | | 12/2003 | Mitsumoto et al. |
| 6,713,036 B1 | | 3/2004 | Vanden Bussche et al. |
| 6,840,256 B1 | | 1/2005 | Ryan et al. |
| 6,953,495 B2 | | 10/2005 | Schwab |
| 7,108,838 B2 | | 9/2006 | McGee |
| 2002/0170429 A1 | * | 11/2002 | Flippo et al. ...................... 95/45 |
| 2003/0021182 A1 | | 1/2003 | Illy et al. |
| 2003/0175183 A1 | | 9/2003 | Guetlhuber |
| 2004/0062689 A1 | | 4/2004 | Gauthier et al. |
| 2005/0234278 A1 | * | 10/2005 | van Egmond et al. ........ 585/324 |
| 2006/0036106 A1 | | 2/2006 | Mazanec et al. |
| 2006/0231645 A1 | | 10/2006 | Chan |

FOREIGN PATENT DOCUMENTS

| | | |
|---|---|---|
| EP | 0026827 | 4/1981 |
| EP | 1705167 | 9/2006 |
| EP | 1726355 | 11/2006 |
| GB | 672446 | 5/1952 |
| GB | 705176 | 3/1954 |
| GB | 1262436 | 2/1972 |
| GB | 1368922 | 10/1974 |
| GB | 2009174 | 6/1979 |
| GB | 2357318 | 6/2001 |
| JP | 55061927 A | 5/1985 |
| JP | 55064579 A | 5/1985 |
| TW | 59083 | 6/2004 |
| WO | WO01/85873 | 11/2001 |
| WO | WO2007/045457 | 4/2007 |
| WO | WO2009/078897 | 6/2009 |
| WO | WO2009/078898 | 6/2009 |
| WO | WO2009/078899 | 6/2009 |
| WO | WO2009/102311 | 8/2009 |

OTHER PUBLICATIONS

PCT International Preliminary Report on Patentability, PCT International Application No. PCT/US2008/012714, mailed Jun. 24, 2010.
Burkholz, Armin, "Droplet Separation", 1989, pp. 180-182, VCH Publishers, New York, NY.
U.S. Appl. No. 12/678,257, Low Shear Gas Mixer, filed Mar. 15, 2010.
U.S. Appl. No. 12/678,270, Oxygen/Hydrocarbon Rapid (High Shear) Gas Mixer, Particularly for the Production of Ethylene Oxide, filed Mar. 15, 2010.
U.S. Appl. No. 12/678,274, Hydrocarbon/Oxygen Industrial Gas Mixer With Water Mist, filed Mar. 15, 2010.
U.S. Appl. No. 12/678,276, Hydrocarbon/Oxygen Industrial Gas Mixer With Coarse Water Droplet Environment to Reduce Ignition Potential, filed Mar. 15, 2010.
Canadian Examiner's Report for Canadian Patent Application No. 2,701,527, dated Nov. 16, 2010.
Communication pursuant to Article 94(3) EPC for Application No. 08 861 507.5, dated Feb. 7, 2011.
Examination Report for GCC/P/2008/12276, GCC Patent Office, dated Feb. 22, 2011.
U.S. Appl. No. 12/678,257, Office Action mailed Mar. 16, 2012.
U.S. Appl. No. 12/678,270, Office Action mailed Jul. 12, 2012.
U.S. Appl. No. 12/678,274, Office Action mailed Jul. 16, 2012.
U.S. Appl. No. 12/678,276, Office Action mailed May 15, 2012.
U.S. Appl. No. 12/678,257, Response to Office Action mailed Mar. 16, 2012, filed Jun. 15, 2012.
Mawhinney et al., Halon Options Technical Working Conference, Protecting Against Vapor Explosions With Water Mist, 215-226, May 2-4, 2000.
U.S. Appl. No. 12/678,257, Office Action mailed Aug. 17, 2012.
PCT International Preliminary Report on Patentability, PCT International Application No. PCT/US2008/012715, mailed Mar. 29, 2010.
PCT International Search Report, PCT International Application No. PCT/US2008/012587, mailed Feb. 10, 2009.
PCT International Search Report, PCT International Application No. PCT/US2008/012716, mailed Oct. 5, 2009.
PCT International Search Report, PCT International Application No. PCT/US2008/012715, mailed Feb. 3, 2009.
PCT International Search Report, PCT International Application No. PCT/US2008/012714, mailed Mar. 10, 2009.
PCT International Search Report, PCT International Application No. PCT/US2008/012586, mailed Feb. 11, 2009.
PCT Written Opinion, PCT International Application No. PCT/US2008/012587, mailed Feb. 10, 2009.
PCT Written Opinion, PCT International Application No. PCT/US2008/012716, mailed Oct. 5, 2009.
PCT Written Opinion, PCT International Application No. PCT/US2008/012715, mailed Nov. 19, 2009.
PCT Written Opinion, PCT International Application No. PCT/US2008/012714, mailed Mar. 10, 2009.
PCT Written Opinion, PCT International Application No. PCT/US2008/012586, mailed Feb. 11, 2009.
PCT International Preliminary Report on Patentability, PCT International Application No. PCT/US2008/012587, mailed Feb. 22, 2010.
PCT International Preliminary Report on Patentability, PCT International Application No. PCT/US2008/012586, mailed Feb. 22, 2010.

* cited by examiner

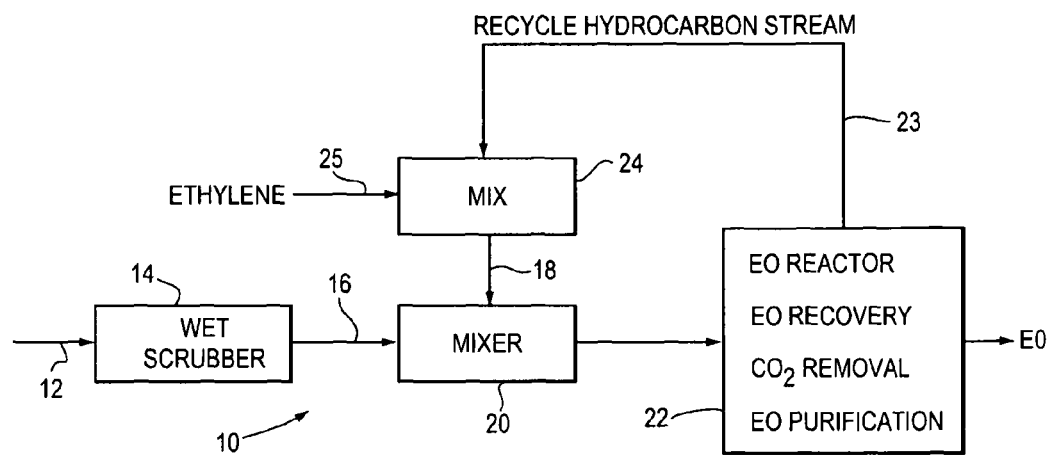
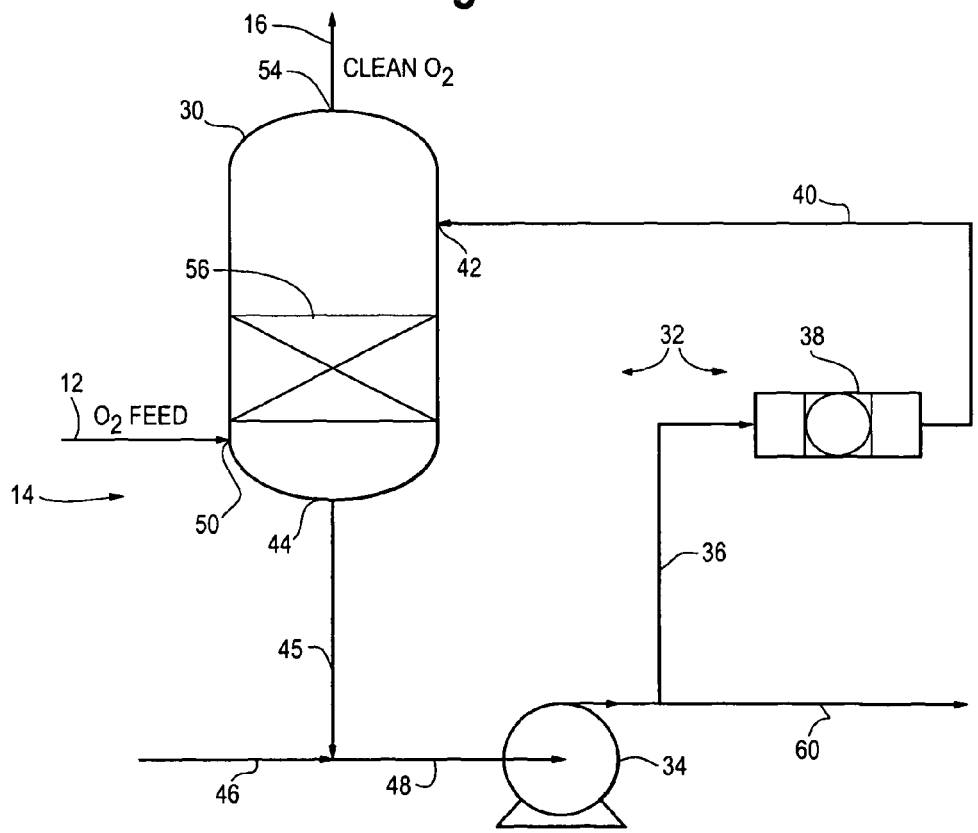

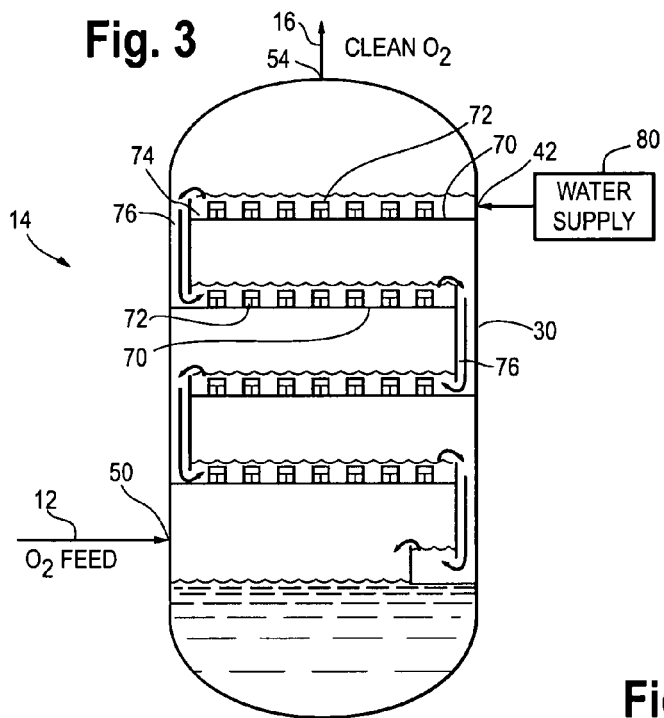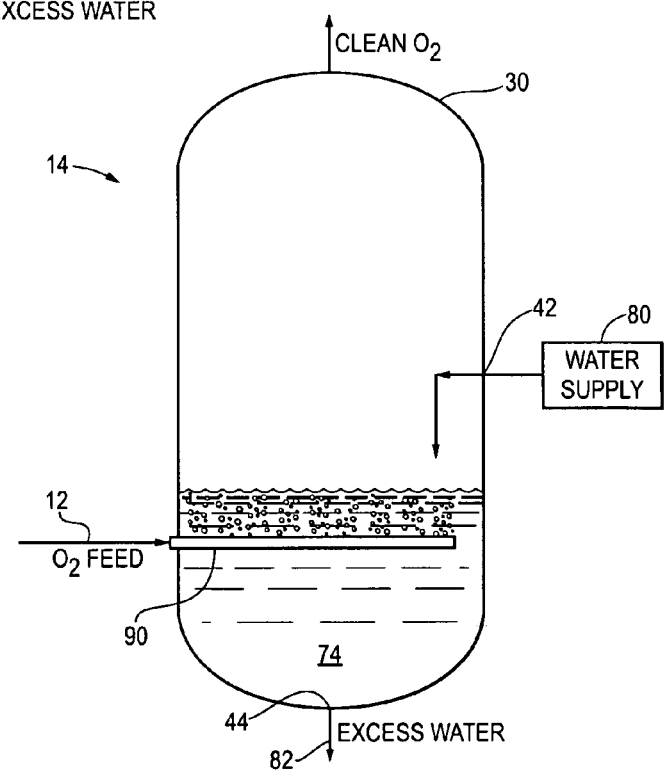

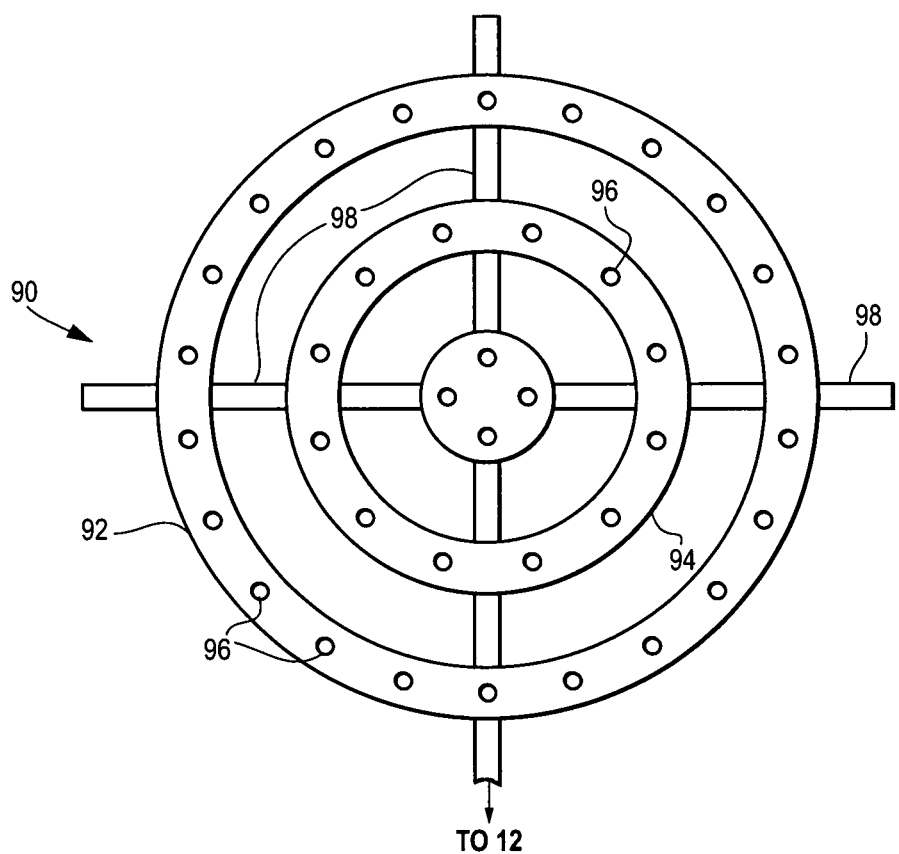

WET SCRUBBING FOR REMOVING PARTICULATE SOLIDS FROM OXYGEN SUPPLY LINE

CROSS-REFERENCE TO RELATED APPLICATIONS

This application is a U.S. National Phase of International Application No. PCT/US2008/012715, filed Nov. 12, 2008, which claims priority to U.S. Provisional Application No. 61/007,671, filed Dec. 14, 2007, all of which are herein incorporated by reference in their entirety.

BACKGROUND

This invention relates generally to systems for production of a gas from a mixture of an oxygen-containing gas stream and a hydrocarbon-containing gas stream. An example of where this invention has utility is systems for industrial production of ethylene oxide.

The chemical compound ethylene oxide (chemical formula $C_2H_4O$) is an important industrial chemical used as an intermediate in the production of ethylene glycol (the main component of automotive antifreeze) and other chemicals. Ethylene oxide is also used as a sterilant for foods and medical supplies. It is a colorless flammable gas at room temperature, and can be cooled and stored as a liquid.

Ethylene oxide first achieved industrial importance during World War I as a precursor to both ethylene glycol and the chemical weapon mustard gas. In 1931, Theodore Lefort, a French chemist, discovered a means to prepare ethylene oxide directly from ethylene and oxygen, using silver as a catalyst. Since 1940, almost all ethylene oxide produced industrially has been made using this method.

In current industrial processes, ethylene oxide is produced when ethylene ($CH_2\!=\!CH_2$) and oxygen ($O_2$) react on a silver catalyst at 200-300° C. showing large Ag nanoparticles supported on Alumina. Typically, chemical modifiers such as chlorine are also included. Pressures used are in the region of 1-2 MPa. The chemical equation for this reaction is:

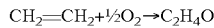

$$CH_2\!=\!CH_2 + \tfrac{1}{2}O_2 \rightarrow C_2H_4O$$

In ethylene oxide production systems, a gas mixer is used to mix the hydrocarbon and oxygen gas streams just upstream of the reaction chamber where the silver catalyst is present. The gas mixer is typically constructed in the form of a vessel or pipe. The vessel includes an inlet manifold for each of the two gases. The vessel is sometimes constructed with a main outer pipe containing the hydrocarbon-containing gas stream and internal concentric tubes or "fingers" which contain the oxygen stream. Mixing occurs at the point where the internal tubes end, where the oxygen gas flowing out of the fingers meets the main stream of hydrocarbon-containing gas flowing in the outer tube. This basic design is described in U.S. Pat. No. 3,706,534.

The art has long recognized that there is a risk of ignition of a hydrocarbon-containing gas stream (e.g., a stream of gas containing for example ethylene mixed with other hydrocarbon gases) at the point where it is combined with an oxygen gas in a gas mixer. Ignition can occur when a particle (e.g. a piece of rust or pipe scale) entrained in the hydrocarbon or oxygen gas stream strikes a metallic surface in the mixer, e.g., the wall of the mixer, thereby producing a spark. If the spark occurs in the hydrocarbon stream in an area of high concentration of oxygen, e.g., at, or close to, the point of mixing of the two gas streams, ignition can occur. The ignition damages the gas mixer and also requires an interrupt of production to suppress the ignition and allow the gas mixer to cool before recommencing production. The flammable region is confined to the mixing zone of the two gases. The hydrocarbon gas as well as the reactor feed blend are below the lower $O_2$ flammability limit—i.e., too rich to burn.

The art has devised a variety of gas mixer designs. Some of the designs are specifically directed to reducing the risk of ignition of hydrocarbon and oxygen gas stream. The known prior art includes the following patent documents, in addition to the above-cited '534 patent: U.S. Pat. No. 4,573,803; U.S. Pat. No. 3,702,619; U.S. Pat. No. 4,256,604; U.S. Pat. No. 4,415,508; U.S. Pat. No. 6,657,079; U.S. 2003/0021182; U.S. Pat. No. 3,518,284; U.S. Pat. No. 4,390,346; U.S. Pat. No. 3,237,923; U.S. Pat. No. 3,081,818; U.S. Pat. No. 2,614,616 and U.S. Pat. No. 6,840,256.

Oxygen supply lines contain particles that can cause ignition hazards. The hazards include sand, dust, metal, and partially oxidized metal particles, although other inert contaminants may pose hazards. At one extreme, impact of large particles, about 100 to 2000 microns, may cause the metal that forms the oxygen piping, valves, and flow control equipment to ignite. At the other extreme, small particles of about 5-1000 microns may cause ignition in the mixers of partial oxidation processes such as ethylene oxide and glycol, or related partial processes using high purity oxygen. It is common practice to use strainers in oxygen supply lines to remove large particles. These do not remove the small particles that can cause mixer fires. Smaller particles down to about 10 microns may be removed using fine filters, but this creates other problems. The filters are liable to clog and are at risk of ignition due to spontaneous ignition or frictional heating, which can cause a fire in the oxygen supply line. The latter is typically caused by poor maintenance or loosening of components over time, creating rubbing of the metal components of the filter.

Additionally, the current practice of filtration and strainers accumulates and concentrates contaminants in the device. This also necessitates periodic cleaning and removal of particulate that has been captured. Pleated metal, ceramic, or mineral wool filter elements collect the particulate. Often the filter housing will contain a number of filter elements operating with parallel flow paths. When the filters collect sufficient material, current practice is to briefly shut the plant down to clean the filter elements. The concentrated particulate can be a source of kindling material for an oxygen fire. These manual operations expose people to hazards. In addition, removing particulate of smaller sizes, such as in the range of 5-30 microns requires more complex and costly filtration devices.

Other prior art of interest include the following patents directed to wet scrubbing technology: U.S. Pat. No. 6,231,648; U.S. Pat. No. 4,012,469; U.S. Pat. No. 5,178,654 and U.S. Pat. No. 5,250,267. Wet scrubbers have been used heretofore in several applications, including mining, semiconductor fabrication, and others, such as for example to remove coal dust, toxic or flammable gases or other contaminants, e.g., sulfur compounds, from a supply of air which is to be released into the environment. To the knowledge of the inventors, wet scrubbing technology has not been previously adopted in ethylene oxide or related production systems.

This disclosure solves a long-felt need in the art for a solution to the problem of removal of particles down to about 5 microns size in an oxygen supply line, while not concentrating the particles, and avoiding problems with clogging or ignition of filters in the oxygen supply lines. Furthermore, production systems using the features of this disclosure avoid the need for a process shutdown to manage the accumulated particulate in screens or filters. Furthermore, it provides for methods of eliminating particulate matter without accumulating material that may be a source of material for a fire in the oxygen supply line.

SUMMARY

The present disclosure is directed to systems for industrial production using oxygen containing gases or enriched air supplies. The invention features the use of one or more wet scrubbing systems in the oxygen supply line to remove particles from the oxygen stream. The wet scrubbing system transfers these particles to an aqueous phase. In particular, wet scrubbing technology transfers solid particles from the gas phase to a water film and phase by diffusion and impaction. The particles become entrained in water which flows through the wet scrubber and are removed from the wet scrubber as a suspension. This provides an environment where the oxygen stream is made essentially particulate free without increasing the potential of a fire in the gas mixer in a partial oxidation process such as the production of ethylene oxide. Particles are removed from the system in the water phase. The particulate concentration in the preferred scrubbing liquid, water, is managed by removing the particles from the system with a combination of filters to remove large particles and purging the scrubbing fluid to remove small particles. Water can be passed through the wet scrubber in either a single pass or in a recirculation loop with appropriate purging and filtering of the recirculated water.

One primary application of the invention is an ethylene oxide production process, in which oxygen is mixed at an intermediate pressure (~20 bar) with recycled flammable gas containing ethylene and other gases. The invention can similarly be used for other partial oxidation processes using pure oxygen or enriched air supplies.

This invention greatly improves the safety of the oxygen injection system into the recirculation stream of ethylene in a gas mixer by removing an ignition source of entrained particulate matter in the oxygen supply. Water scrubbing as a class of particulate removal is advantageous for coupling to the ethylene oxide process (and other hydrocarbon/oxygen gas mixing processes) because particulates are removed and never concentrated. As noted above, current best practice is to use filters on the incoming oxygen supply. However, these filters collect and concentrate the particulate that has been itself a cause of ignition events. Coupling a wet scrubber to the oxygen supply obviates the need for filters in the oxygen supply line and thus avoids problems associated therewith. Furthermore, the wet scrubber can be readily designed to remove particulate having a size in the range of 5-1,000 microns, i.e., particle sizes which present particular risks of ignition in an ethylene oxide gas mixer. Because these particles are removed, the risks of ignition in the gas mixer are substantially reduced.

Thus, in one aspect of this disclosure, an improvement is provided to a system for production of ethylene oxide, the system including an oxygen supply line for carrying a stream of oxygen gas and a gas mixer where the oxygen gas is mixed with a hydrocarbon-containing gas stream, the improvement comprising providing a wet scrubber in the oxygen supply line, the wet scrubber removing particulate matter from the stream of oxygen gas wherein scrubbed oxygen (particulate free) gas is supplied to the gas mixer.

In another aspect, a method is provided for mixing an oxygen gas with a hydrocarbon gas, comprising the steps of: wet scrubbing the oxygen gas in a wet scrubber; supplying oxygen gas from the wet scrubber to a gas mixer; and mixing the oxygen gas with the hydrocarbon gas in the gas mixer.

A variety of wet scrubber constructions are suitable for use in the inventive methods. Several preferred constructions will be described in some detail. These include packed-tower, bubble cap, jet-type, and sparger-type wet scrubbers.

BRIEF DESCRIPTION OF THE DRAWINGS

FIG. 1 is a diagram of a gas production system featuring a wet scrubber in the oxygen supply line, a gas mixer and a reaction chamber downstream of the gas mixer. The system of FIG. 1 may be used in industrial production of ethylene oxide.

FIG. 2 is a more detailed illustration of one embodiment of the wet scrubber of FIG. 1, with the wet scrubber being a "packed tower"-type wet scrubber.

FIG. 3 is a more detailed illustration of an alternative embodiment of the wet scrubber of FIG. 1, with the wet scrubber being a "bubble cap"-type wet scrubber.

FIG. 4 is a more detailed illustration of an alternative embodiment of the wet scrubber of FIG. 1, with the wet scrubber being a sparger-type wet scrubber.

FIG. 5 is a plan view of the sparger of FIG. 4.

DETAILED DESCRIPTION

FIG. 1 is a diagram of a production system 10 which, for purposes of explanation and not limitation, is an ethylene oxide production system. The principles of the present invention will be applicable to other production systems as will be apparent from the following description.

The system 10 includes an oxygen supply line 12 carrying a stream of oxygen gas from a source (not shown). The oxygen supply line includes entrained particulate matter, such as sand, rust, pipe scale, typically in the range of 5-1000 microns in size. The system may include an optional in-line strainer (not shown) to remove very large particles or foreign matter. The system 10 features a wet scrubber 14 which functions to remove most or more preferably substantially all of the particulate matter in a given size range (5-1000 microns in one embodiment) from the stream of oxygen gas. Scrubbed oxygen gas is supplied along a pipe 16 to a gas mixer 20. The pipe 16 is preferably made from a scale and corrosion resistant material, such as stainless steel or Monel.

A second pipe 18 carries a hydrocarbon-containing gas stream to the gas mixer 20. The hydrocarbon-containing gas stream (containing ethylene gas and possibly other hydrocarbon gases in this example) is mixed with the oxygen gas stream in the gas mixer 20. The resulting mixed gases are fed to a reaction chamber 22 containing a catalyst. A reaction occurs between the two gases in the reaction chamber 22. The resulting reaction product (e.g., ethylene oxide ("EO")) is fed from the reaction chamber 22 to a recovery train and storage facility or a downstream reactor or production facility. The reaction chamber 22 (or downstream reaction facilities) may include facilities EO recovery, $CO_2$ removal, and EO purification. Hydrocarbon gases are recovered from the reaction chamber 22 and recycled via line 23 to a mixer 24 where they are mixed with ethylene gas along line 25. Thus, the gas injected into the mixer 20 on line 18 contains ethylene gas and other hydrocarbon gases in this example.

The use of the wet scrubber 14 in the oxygen supply line 12 overcomes many problems which have plagued the art for many years. In particular, it achieves the goal of removal of particles from the oxygen supply line, while not concentrating the particles and avoiding problems with clogging or ignition of filters in the oxygen supply lines 12. Furthermore, the wet scrubber 14 can perform the scrubbing task continuously, avoiding the need for a process shutdown to manage the accumulated particulate in screens or filters. Additionally, it eliminates particulate matter from the oxygen feed, without accumulating material that may be a source of "kindling" material for a fire in the oxygen supply line 12.

The particular details of the construction of the wet scrubber may vary widely depending on the needs or requirements of the particular industrial process that is involved. Wet scrubbers for particulate systems suitable for this disclosure have been well studied. Several well characterized wet scrubber systems for particulate removal are illustrated in FIG. 11-6 of Armin Burkholz's book "Droplet Separation" VCH Publishers, New York (1989), which is incorporated by reference herein. These systems include packed tower, jet scrubber, swirl scrubber, rotary scrubber and venturi scrubber systems. The simple packed tower can readily be designed to achieve 95% removal of particles above 1.5 micron diameter for a particle density of 2.4 grams per cubic centimeter. FIG. 11-7 of the Burkholz book shows the experimental fractional separation efficiency curves for different types of scrubbers for dust particles of that particle density at 1 bar (absolute) pressure.

Wet scrubber systems transfer the particulate matter to a water stream that is flowed through the scrubber 14. The particulate matter can either be purged or filtered from the liquid. There is some operational complexity associated with start-up and shut down of the wet scrubber. In addition, the water stream will be super-oxygenated, thus the alloys chosen for the wet scrubber must resist corrosion in this environment. Preferably, the water used in the wet scrubber is conditioned water in which dissolved salts are substantially removed from the water. For example, the conditioned water is a steam condensate (distilled water).

The wet scrubber 14 may include the following elements: a system oxygen feed, a wet scrubbing particulate removal device (packed tower, jet scrubber, venturi scrubber, or other device), a water recirculation pump, a strainer to remove large particles (optional), a scrubbing liquid (water, and particularly conditioned water being preferred) feed, and a purge of water containing the particulate matter. Smaller diameter particulate will be carried out of the system with the purged liquid that could be optionally filtered. High reliability is required for this system, therefore some of the particulate removal technologies are advantaged due the low complexity level and absence of moving parts, and others are greatly disadvantaged for this application. A rotary scrubber is an example of disadvantaged approach because of the mechanically complexity presented by a rotary contactor device used in such a scrubber.

A typical process requirement for particulate removal in an ethylene oxide production system is removal of particles in the size range of 5 to 1000 microns at an operating pressure of 20-25 bar. This requirement suggests that the less mechanically intensive/complex devices, such as a packed tower, trayed tower, or jet scrubber will achieve the desired results with maximum reliability.

Experimental testing of wet scrubbers by the inventors have resulted in several additional insights on the preferred design of a wet scrubber.

Firstly, very small particles appear to have the ability to attach themselves to quiescent (low-flow) sections of the scrubber vessel, such as on the vessel wall. Over time, these particles could accumulate to a sufficiently large mass such that they could drop off of the wall of the vessel. It is possible that some particles could escape out of the scrubber when a relatively large mass of particles falls off or drops from a surface. To militate against this, an optional feature may be incorporated into the scrubber consisting of an internal network of spray nozzles, connected by water supply piping, that could allow wash water to be sprayed on a prescribed or as-needed basis to wash down the internal walls of the scrubber vessel most likely to accumulate small particles. These locations would be identified during the vessel design to allow the number of spray nozzles and their orientation to be optimized.

Secondly, to further reduce the potential for small particles to escape from the scrubber in water mist or entrainment out of the top of the scrubber, another optional feature which can be added to the scrubber is a mist eliminator or cycle separator at the top (vapor outlet) of the scrubber vessel. A suitable mist eliminator could be made of wire mesh or metal vanes.

Thirdly, we haven noticed that it appears that very small (<100 micron) particles may accumulate in a film on top of the water surface (e.g., in the design of FIG. 3 or 4 discussed below). This observation led to the insight to add a small amount of a surfactant (<500 ppmw) in the scrubbing water to enhance the removal of very small particles by keeping them in suspension in the scrubbing water. The surfactant should be chemically compatible with the oxygen gas stream.

Example 1

FIG. 2 is a more detailed illustration of one embodiment of the wet scrubber 14 of FIG. 1, with the wet scrubber being a "packed tower"-type wet scrubber.

The wet scrubber of FIG. 2 includes a vessel 30 containing a packing material 56 (most advantageously ceramic but optionally metallic) and a water circulation loop 32. The circulation loop 32 includes a pump 34, a recirculation line 36, a strainer 38, an inlet line 40 and a water inlet 42. Water flows down over the packing material 56. Entrained particulate matter is collected with the water and removed via a water outlet 44. The line 45 carries water to a mixing point 48 where makeup water carried along line 46 is mixed with water from line 45. The circulation pump 34 circulates water through the loop 32. Line 60 is a purge line where the particulate is discharged.

The vessel 30 includes an oxygen feed inlet 50 receiving oxygen from the supply pipe 12 and a clean oxygen outlet 54 supplying clean oxygen gas to outlet pipe 16, which supplies oxygen gas to the gas mixer 20 of FIG. 1. Preferably, the outlet 54 is close coupled to the oxygen/cycle gas mixer 20 and pipe 16 is as short as reasonably feasible, with only isolation and flow control valves between the outlet 54 of the wet scrubbing system and the mixer 20.

As noted, the water circulated in the loop 32 is preferably clean, filtered, deionized, conditioned water in which dissolved salts are substantially removed from the water, such as water obtained from condensation of steam (distilled water).

In a commercial scale implementation in a packed tower type scrubber (FIG. 2), approximately 50,000 kg/hr of oxygen ~+99% purity at a pressure of 20-25 bar is fed through the wet scrubber vessel 30. This oxygen contains particulate impurities such as rust, pipe scale, and sand with particle sizes from 1 to 1000 micron diameter. An optional strainer (not shown) at the inlet 50 to the vessel 30 would remove grossly oversize foreign matter. The make-up water along line 46 must meet the need to saturate to oxygen leaving the system with the water vapor and to make-up for the purged liquid. The purged liquid flow carries the particulate in water at a concentration of 0 to 1%. The design of the packed bed 56 follows known practice which results in a column diameter of ~1 m. In this configuration, a recirculation pump 34 is shown for a packed tower that would have 1 meter of packing depth with 10 to 20 mm ceramic or stainless steel saddles as a packing material 56. An optional strainer 38 in the liquid recirculation line 36 would capture large particulates that may foul the packing material. Conditioned water such as polished steam condensate is the preferred scrubbing liquid, due to the minimum amount of dissolved salts.

The design of FIG. 2 could also be fitted with spray nozzles to wash the interior walls of the vessel 30, a mist eliminator at the outlet 54, and/or the scrubbing water could be augmented by a small amount of a surfactant compatible with the oxygen gas stream.

Example 2

FIG. 3 is a more detailed illustration of an alternative embodiment of the wet scrubber 14 of FIG. 1, with the wet scrubber being a "bubble cap" wet scrubber.

The design of FIG. 3 features a vessel 30 having a water inlet 42 for receiving a supply of water from a water supply 80, and a water outlet 44 for discharge of purge water, a gas inlet 50 for receiving an oxygen feed supply from pipe 12 and a gas outlet 54 for removal of scrubbed oxygen gas. The vessel 30 includes a plurality of bubble caps 72, basically caps having small openings for oxygen gas to egress through the cap. The vessel 30 includes water containment features in the form of trays 70 for supporting a flow of water over the bubble caps 72. The bubble caps 72 receive oxygen gas from the gas inlet 50 via internal conduits (not shown). The water is present over the trays 70 at a level which completely covers the bubble caps. The oxygen gas is ejected through the openings in the bubble caps and bubbled through the water flowing over the bubble caps. Entrained particulate matter in the oxygen gas is captured by the flow of water and removed from the vessel 30 via the water outlet 44.

The trays 70 are shown arranged within the vessel 30 in a plurality of vertically-stacked trays supporting a flow of water 74 over the bubble caps 72. The water inlet 42 is positioned within the vessel 30 at or above the top-most tray 70 as shown in FIG. 3. At start-up, the water 74 fills up the uppermost tray 70 and then flows over the edge down a downcomer 76 to the tray below, fills the tray below to a level at which the bubble caps 72 are submerged in water, flows over the downcomer 76 to the tray below, etc. Eventually all the trays are completely filled with water submerging the bubble caps, and water accumulates in the bottom of the vessel 30 at the rate at which it is introduced into the top 42, minus the rate at which water which is absorbed into the gas stream and conducted out of the vessel.

In an example of a commercial production system, dry oxygen gas flows into the vessel 30 at a rate of 50,000 kg/hr. Clean, filtered, conditioned water is introduced at the inlet 42 at a rate of 500 kg/hr. Excess water is removed from the vessel on line 82 at a rate of approximately 425 kg/hr, with approximately 75 kg/hr water absorbed by the oxygen gas. The vessel in the illustrated embodiment is approximately 3 meters in height, made from stainless steel to withstand 30 bar. The bubble caps 72 are seal welded to the trays 70. The diameter of the vessel is approximately 1.3 m. The number of trays and bubble caps can be varied to achieve the degree of particulate removal that is desired.

The design of FIG. 3 has a low liquid flow requirement and can be constructed as a single pass system, i.e., it does not require any recirculation loop in the water system. This presents some advantages over other wet scrubbing systems. Additionally, the design of FIG. 3 is economical, easy to retrofit into existing production systems, is of minimal complexity, has no moving parts, and is reliable. The system is also effective at scrubbing particulate matter in the size range of 5-1,000 microns.

In one possible variation, the embodiment of FIG. 3 is modified to include a recirculation loop in the water system. Water is circulated from the water outlet 44 to the water inlet 42, and a filter or strainer is placed in a line connecting the water outlet to the water inlet. The recirculation loop would include a mixing point to add make-up water into the loop to account for absorption of water in the oxygen gas and any purging of the water loop. The purge stream in line 82 would remove particulate matter with the purge water. The recirculation loop would permit the use of higher capacity commercial trays, which would reduce the column diameter relative to the bubble cap design.

As with the case in Example 1, the design of Example 2 preferably places the wet scrubber 14 close to the gas mixer 20 with only the isolation and flow control valves between the outlet of the wet scrubber 14 and the inlet to the mixer 20.

The design of FIG. 3 could also be fitted with spray nozzles to wash the interior walls of the vessel 30, a mist eliminator at the outlet 54, and/or the scrubbing water could be augmented by a small amount of a surfactant compatible with the oxygen gas stream.

Example 3

FIG. 4 is a more detailed illustration of an alternative embodiment of the wet scrubber of FIG. 1, with the wet scrubber 14 being a sparger-type wet scrubber. The wet scrubber 14 of FIG. 4 includes a vessel 30, a water supply 80 supplying water to a water inlet 42, a water outlet 44 and a drain line for purge water 82. The oxygen is supplied from the pipe 12 to a sparger 90. Clean, filtered, conditioned water 74 is introduced into the vessel 30 and fills the vessel 30 to a level which completely covers the sparger 90, as shown. The sparger 90 is shown in a plan view in FIG. 5. The sparger 90 includes an arrangement of hollow tubes 92 and 94 containing the oxygen gas. The tubes 92, 94 have small holes 96 through which the oxygen gas flows due to the gas pressure within the tubes. The sparger includes supports 98 which are affixed to the walls of the vessel to support the sparger 90 within the vessel 30. Oxygen gas flowing out of the holes 96 is bubbled through the water 74, with the entrained particulate matter being transferred to the water 74. The size of the bubbles in the water 74 is related to the orifice 96 size of the sparger.

In an example of a commercial production system, dry oxygen gas flows into the vessel 30 at a rate of 50,000 kg/hr. Clean, filtered, conditioned water is introduced at the inlet 42 at a rate of 500 kg/hr. Excess water is removed from the vessel at a rate of approximately 425 kg/hr, with approximately 75 kg/hr water absorbed by the oxygen gas and removed from the vessel with the gas. The vessel in the illustrated embodiment is approximately 3 meters in height, 1.3 m in width, and made from stainless steel in a design to withstand 30 bar.

The design of Example 3 is also advantageous in many applications because it is a simple design with no moving parts, and does not require a recirculation loop for the water. An alternative embodiment would include a recirculation loop and filter or screen, make up mixing point, and purge for removal of water from the recirculation loop.

As with the case in Example 1, the design of Example 3 preferably places the wet scrubber close to the gas mixer 20 with only the isolation and flow control valves between the outlet of the wet scrubber 14 and the inlet to the mixer 20.

The design of FIG. 4 could also be fitted with spray nozzles to wash the interior walls of the vessel 30, a mist eliminator at the clean O2 gas outlet at the top of the vessel 30, and/or the scrubbing water could be augmented by a surfactant compatible with the oxygen gas stream.

From the above discussion, it will be appreciated that the Examples disclosed above, taken in conjunction with FIG. 1, have demonstrated a method of mixing an oxygen gas with a hydrocarbon-containing gas, comprising the steps of: wet scrubbing the oxygen gas in a wet scrubber 14; supplying oxygen gas from the wet scrubber 14 to a gas mixer 20, and mixing the oxygen gas with the hydrocarbon-containing gas in the gas mixer. The gas mixer 20 may take the form of the gas mixers described in the previously cited patent documents. In one embodiment, the hydrocarbon-containing gas comprises ethylene gas. As examples of other embodiments, the hydrocarbon-containing gas contains methane gas, or $N_2$ ballast gas. However, the method may be used in conjunction with other processes using other hydrocarbon gases. Preferred embodiments of the method provide for removal of particulate matter in the wet scrubber having a size in the range of 5-1,000 microns. The wet scrubber technology is also effective for capturing smaller particles down to submicron size, however this is not deemed necessary for the disclosed E-O gas mixing application.

Even more generally stated, the features of this disclosure provide an improvement to any partial oxidation system (of which ethylene oxide production is but one example) having an oxygen supply line carrying a stream of oxygen gas. The improvement takes the form of providing a wet scrubber in the oxygen supply line, the wet scrubber removing particulate matter from the stream of oxygen gas.

The water used in the wet scrubbers of this disclosure will typically be at ambient temperature.

While presently preferred embodiments have been described with particularity, variation from the specifics of the disclosed embodiments may be made without departure from the scope of the invention. All questions concerning scope of the invention are to be determined by reference to the appended claims.

We claim:

1. In a system for production of ethylene oxide, the system including an oxygen supply line for carrying a stream of oxygen-containing gas and a gas mixer where the oxygen gas is mixed with ethylene-containing gas, the improvement comprising:
    providing a wet scrubber in the oxygen supply line, the wet scrubber removing particulate matter from the stream of oxygen containing gas wherein scrubbed oxygen gas is supplied to the gas mixer.

2. The improvement of claim 1, wherein the wet scrubber comprises a packed tower-type wet scrubber.

3. The improvement of claim 1, wherein the wet scrubber comprises a bubble-cap type wet scrubber.

4. The improvement of claim 1, wherein the wet scrubber comprises a sparger-type wet scrubber.

5. The improvement of claim 1, wherein the wet scrubber comprises a jet scrubber.

6. The improvement of claim 2, wherein the packed tower-type scrubber comprises:
    a vessel containing a packing material, an oxygen feed inlet and a clean oxygen outlet;
    a circulation pump; and
    a water loop containing water circulated by the circulation pump, the water loop including the vessel, a strainer upstream of the vessel, and a mixing point for introducing make up water into the loop.

7. The improvement of claim 3, wherein the bubble-cap type wet scrubber comprises:
    a vessel having a water inlet for receiving a supply of water and a water outlet for removal of excess water, a gas inlet for receiving an oxygen feed supply and a gas outlet for removal of scrubbed oxygen gas;
    a plurality of bubble caps within the vessel having water containment features for supporting a flow of water over the bubble caps, wherein the bubble caps receive oxygen gas from the gas inlet;
    wherein oxygen gas is passed through the bubble caps and bubbled through the water flowing over the bubble caps, and entrained particulate matter in the oxygen gas is captured by the flow of water and removed via the water outlet.

8. The improvement of claim 7, wherein the bubble caps are arranged within the vessel in a plurality of vertically-stacked trays supporting a flow of water over the bubble caps, wherein the water inlet is positioned within the vessel at or above the top-most tray, and wherein the water containment features include downcomers for flow of water down from one tray to the next within the vertically-stacked trays.

9. The improvement claim 7, wherein the water is circulated from the water outlet to the water inlet, and wherein a filter is placed in a line connecting the water outlet to the water inlet.

10. The improvement claim 7, wherein the water is circulated in a single pass through the vessel.

11. The improvement claim 1, wherein the wet scrubber is closely coupled to the gas mixer.

12. The improvement claim 1, wherein the wet scrubber includes at least one of a) one or more sprayers for spraying an internal wall of the wet scrubber, b) a mist eliminator at an oxygen gas outlet of the scrubber, and c) a surfactant is added to water supplied to the wet scrubber.

13. A method of mixing an oxygen containing gas with a hydrocarbon containing gas, comprising the steps of:
    wet scrubbing the oxygen gas in a wet scrubber;
    supplying oxygen containing gas from the wet scrubber to a gas mixer;
    mixing the oxygen containing gas with the hydrocarbon containing gas in the gas mixer.

14. The method of claim 13, wherein the hydrocarbon-containing gas comprises ethylene gas.

15. The method of claim 13, wherein the wet scrubber comprises a packed tower-type wet scrubber.

16. The method of claim 13, wherein the wet scrubber comprises a bubble-cap type wet scrubber.

17. The method of claim 13, wherein the wet scrubber comprises a sparger-type wet scrubber.

18. The method of claim 13, wherein the wet scrubber comprises a jet scrubber-type wet scrubber.

19. The method claim 13, wherein the wet scrubber includes at least one of a) one or more sprayers for spraying an internal wall of the wet scrubber, b) a mist eliminator at an oxygen gas outlet of the wet scrubber, and c) a surfactant is added to water supplied to the wet scrubber.

* * * * *